US00PP26643P3

(12) United States Plant Patent
Caster et al.

(10) Patent No.: US PP26,643 P3
(45) Date of Patent: Apr. 26, 2016

(54) BLUEBERRY PLANT NAMED 'DRISBLUETEN'

(50) Latin Name: ***Vaccinium corymbosum* L.**
Varietal Denomination: DrisBlueTen

(71) Applicant: DRISCOLL STRAWBERRY ASSOCIATES, INC., Watsonville, CA (US)

(72) Inventors: Brian K. Caster, Salinas, CA (US); Arlen Draper, Payson, AZ (US); Jennifer K. Izzo, Watsonville, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 175 days.

(21) Appl. No.: 13/998,838

(22) Filed: Dec. 13, 2013

(65) Prior Publication Data

US 2015/0173263 P1 Jun. 18, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Jondle & Associates, P.C.

(57) ABSTRACT

A new and distinct variety of blueberry plant named 'DrisBlueTen' particularly distinguished by having an early harvest season, strong vigor and large, firm berries, is disclosed.

2 Drawing Sheets

Genus and species: *Vaccinium corymbosum* L.
Variety denomination: 'DrisBlueTen'.

BACKGROUND OF THE NEW PLANT

The invention relates to a new and distinct blueberry variety designated 'DrisBlueTen' and botanically known as *Vaccinium corymbosum* L. This new blueberry variety was discovered in Santa Cruz County, Calif. in September 2003 and originated from a cross between the female parent blueberry plant 'Nui' (U.S. Plant Pat. No. 6,699) and the proprietary male parent blueberry plant 'MS122' (unpatented). The original seedling of the new variety was first asexually propagated via softwood cuttings at a nursery in Monterey County, Calif. in 2002. 'DrisBlueTen' was subsequently asexually propagated via softwood cuttings and underwent further testing at a nursery in Santa Cruz County, Calif. for eight years (2005-2012). The present invention has been found to be stable and reproduce true to type through successive asexual propagations via softwood cuttings.

Plant Breeder's Rights for this variety have not been applied for. 'DrisBlueTen' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz County, Calif.

1. Early harvest season;
2. Strong vigor; and
3. Large, firm berries.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are four years old.

DESCRIPTION OF THE NEW CULTIVAR

Figure 1:
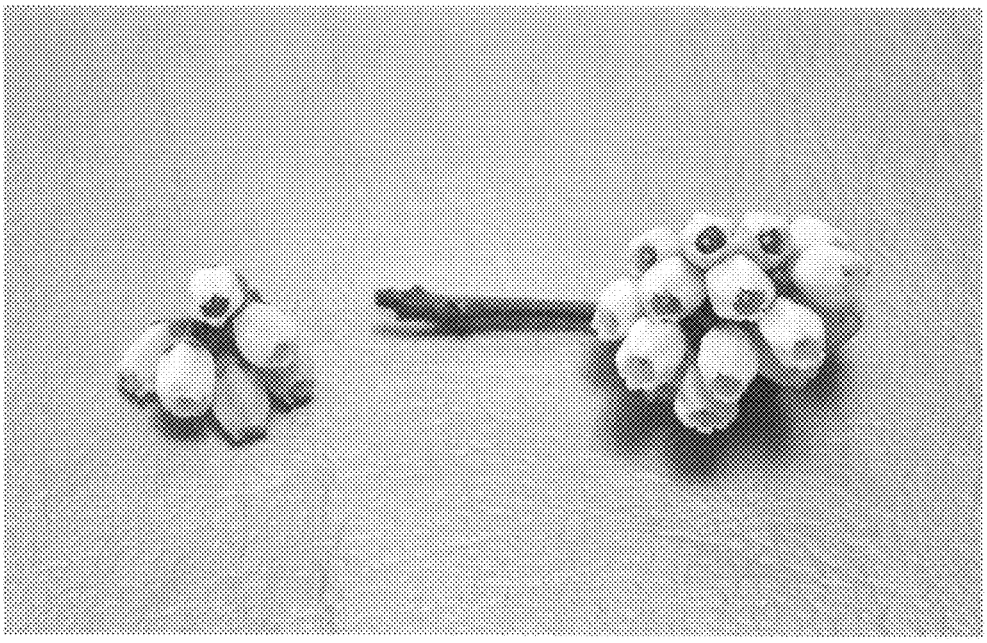
FIG. 1 shows a close-up of the mature flowers.
Figure 2:
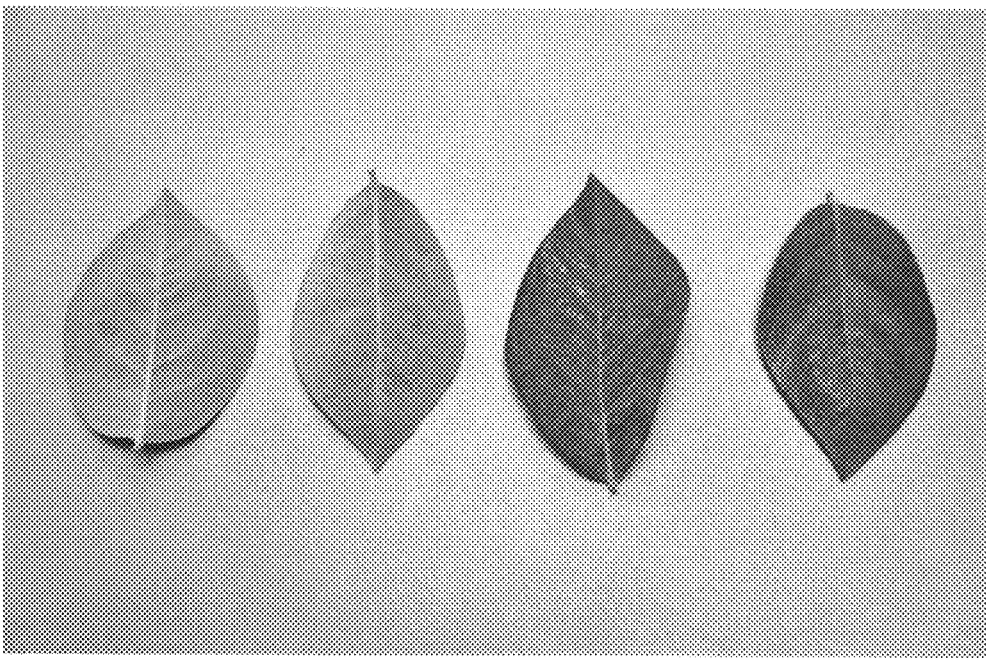
FIG. 2 shows a close-up of the leaves.
Figure 3:
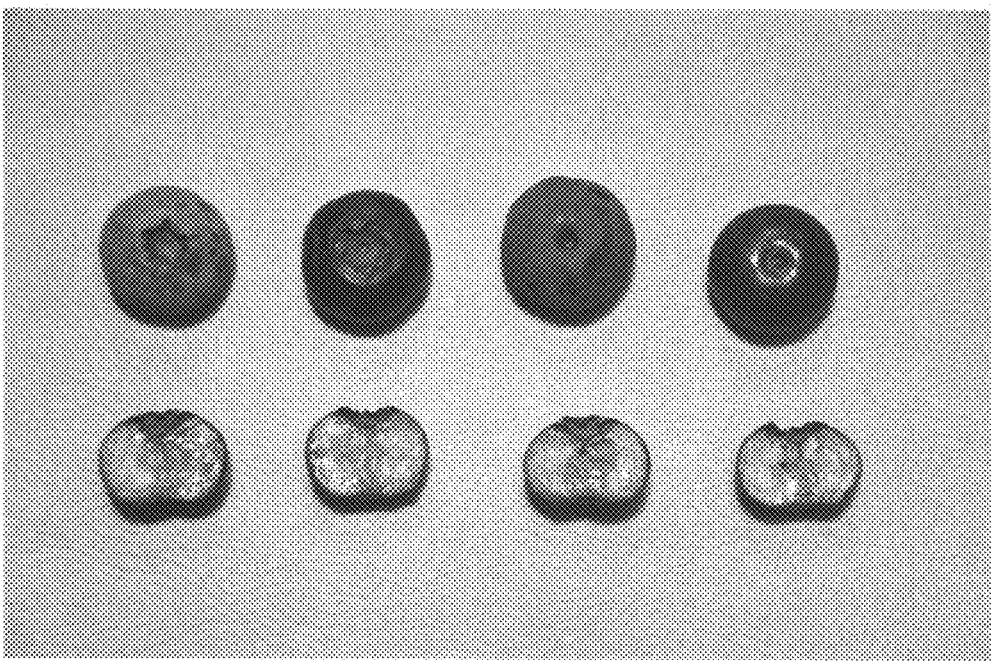
FIG. 3 shows a close-up of the whole fruit and a cross-section of the fruit.

The following detailed description sets forth the distinctive characteristics of 'DrisBlueTen'. The data which define these characteristics is based on observations taken in Santa Cruz County, Calif. from 2005-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueTen' has not been observed under all possible environmental conditions. The botanical description of 'DrisBlueTen' was taken from 4 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family*.—Ericaceae.
*Botanical*.—*Vaccinium corymbosum* L.
*Common name*.—Blueberry.
*Variety name*.—'DrisBlueTen'.

Parentage:

*Female parent*.—The blueberry plant 'Nui' (U.S. Plant Pat. No. 6,699).

*Male parent*.—The proprietary blueberry plant 'MS122' (unpatented).

Plant:

*Size*.—Small.

*Height*.—83.8 cm.

*Width*.—82.0 cm.

*Length/width ratio*.—1.0.

*Plant vigor*.—Strong.

*Growth habit*.—Semi-erect to spreading.

*Productivity*.—Medium.

*Cold hardiness*.—Medium; USDA Plant Hardiness Zone 6.

*Chilling requirement*.—High.

*Propagation*.—Soft wood cuttings.

*Time of vegetative bud burst*.—Medium.

*Fruiting type*.—Only on one-year-old shoots.

*Cane renewal*.—Medium.

*Internode length* (*upper half on one-year old shoot*).—24.8 mm.

*One-year old canes* (*young canes*).—Length: 87.0 cm. Diameter at the base: 8.0 mm. Diameter at the tip: 7.0 mm. Texture: Smooth. Color (One-year old shoot, branch and canes): RHS 152C (Medium yellow-green).

*Five-year old canes* (*mature canes*).—Length: 82.0 cm. Diameter at the base: 18.5 mm. Diameter at the tip: 3.2 mm. Texture: Rough. Color: RHS 197B (Medium greyed-green).

Leaves:

*Length*.—Medium; 5.55 cm.

*Width*.—Medium; 3.65 cm.

*Length/width ratio*.—1.5; Longer than broad.

*Shape*.—Elliptic.

*Apex*.—Cuspidate.

*Base*.—Obtuse.

*Margin*.—Entire.

*Glossiness*.—Medium.

*Pubescence*.—Glabrous (Absent).

*Sheath*.—Absent.

*Arrangement*.—Alternate.

*Venation*.—Reticulate.

*Color*.—Upper surface: Dark; RHS 137A (Dark green). Lower surface: Medium; RHS 146A (Medium yellow-green).

*Internode length* (*one-year old shoot, upper half*).—Short; 17.88 mm.

Petiole:

*Length*.—1.8 mm.

*Diameter*.—1.28 mm.

*Color*.—RHS 145B (Light yellow-green).

Flowers:

*Length* (*excluding peduncle*).—Very long; 10.50 mm.

*Diameter*.—6.93 mm.

*Length/width ratio*.—1.5.

*Color*.—RHS 155D (White).

*Flower bud*.—Length: 4.0 mm. Width: 3.0 mm. Number of flowers per bud or peduncle: 8. Color on immature buds: Dark; RHS 183A (Greyed-purple). Color on mature buds: Medium; RHS 64B (Red-purple).

*Petal width*.—4.71 mm.

*Fragrance*.—Medium.

*Time of beginning flowering on one-year shoot*.—Early.

*Pedicel*.—Length: 7.47 mm. Diameter: 0.86 mm. Color: RHS N144D (Medium yellow-green).

*Corolla*.—Height of corolla tube: 10.5 mm. Diameter of corolla tube: 6.93 mm. Aperture diameter: 4.21 mm. Shape: Urceolate (Urn-shaped). Size of corolla tube: Large. Anthocyanin coloration of corolla tube: Very weak or absent; RHS 155D (White). Ridges on tube: Present.

*Peduncle*.—Length: 18.01 mm. Surface texture: Smooth. Color: RHS N144D (Medium yellow-green).

Reproductive organs:

*Style length* (*including stigma*).—Medium to long; 8.64 mm.

*Style color*.—RHS N144C (Medium yellow-green).

*Ovary color*.—RHS 133C (Medium green).

*Pollination requirement*.—Intermediate.

*Pollen amount*.—Medium.

*Pollen color*.—RHS 8D (Light yellow).

*Anther color*.—RHS 26A (Medium orange).

Fruit:

*Size*.—Large.

*Length*.—11.62 mm.

*Width*.—16.35 mm.

*Length/width ratio*.—0.7.

*Fruit pedicel diameter*.—1.14 mm.

*Weight*.—3.0 g.

*Number of berries per cluster*.—7.20.

*Cluster density*.—Medium.

*Shape in longitudinal sections*.—Oblate.

*Intensity of green color* (*immature fruit with bloom*).—Medium; RHS 191B (Medium greyed-green).

*Color of skin* (*immature fruit without bloom*).—RHS N79A (Dark purple).

*Color of skin* (*mature fruit without bloom*).—RHS 103A (Dark blue).

*Color of skin* (*mature fruit with bloom*).—RHS 104D (Light blue).

*Intensity of bloom* (*mature fruit*).—Strong.

*Attitude of sepals*.—Incurving.

*Calyx*.—Diameter of basin: Medium; 5.56 mm. Depth of basin: Medium; 2.79 mm. Diameter/depth ratio: 2.0.

*Flesh color*.—RHS 145D (Light yellow-green).

*Firmness*.—Medium to firm.

*Sweetness*.—Medium to high.

*Acidity*.—Low to medium.

*Time of beginning of fruit ripening* (*one-year old shoots*).—Early.

*Harvest season*.—Early.

*Harvest interval*.—Late-May to early August.

Seeds:

*Length*.—1.58 mm.

*Width*.—0.77 mm.

*Length/width ratio*.—2.1.

*Abundance*.—Medium.

*Color*.—RHS N167A (Medium greyed-orange).

Resistance to pests and diseases: Data not available.

COMPARISON WITH PARENTAL AND COMMERCIAL VARIETIES

'DrisBlueTen' differs from the female parent 'Nui' (U.S. Plant Pat. No. 6,699) in that 'DrisBlueTen' ripens earlier than 'Nui' and has fruit that is smaller size than 'Nui'.

'DrisBlueTen' differs from the commercial variety 'Elliott' (unpatented) in that 'DrisBlueTen' has large berries with medium to high sweetness, whereas 'Elliott' has medium to large sized berries that are quite tart unless picked fully ripe.

'DrisBlueTen' differs from the commercial variety 'Bluecrop' (unpatented), in that 'DrisBlueTen' has a semi-erect to spreading growth habit, whereas 'Bluecrop' has an upright growth habit. Additionally, 'DrisBlueTen' has an early harvest season, whereas 'Bluecrop' has a mid-season harvest.

We claim:

1. A new and distinct variety of blueberry plant named 'DrisBlueTen' as shown and described herein.

* * * * *